United States Patent [19]
Abushanab

[11] Patent Number: 5,659,021
[45] Date of Patent: Aug. 19, 1997

[54] CHIRAL GLYCEROL DERIVATIVES

[75] Inventor: Elie Abushanab, Peace Dale, R.I.

[73] Assignee: The Board of Governors for Higher Education, State of Rhode Island and Providence Plantations, Providence, R.I.

[21] Appl. No.: 279,836

[22] Filed: Jul. 25, 1994

Related U.S. Application Data

[63] Continuation of Ser. No. 852,885, Mar. 17, 1992, abandoned, which is a continuation of Ser. No. 505,246, Apr. 5, 1990, abandoned, which is a division of Ser. No. 25,624, Mar. 13, 1987, Pat. No. 4,931,575.

[51] Int. Cl.$^6$ .............................. C07H 1/00; C07H 15/02; C07H 15/04; C07H 15/20
[52] U.S. Cl. ........................ 536/1.11; 536/4.1; 536/120; 536/124; 536/125
[58] Field of Search ................. 536/120, 124, 536/122, 125, 4.1, 1.11

[56] References Cited

U.S. PATENT DOCUMENTS

| | | | |
|---|---|---|---|
| 4,145,531 | 3/1979 | Eckstein et al. | 536/24 |
| 4,206,291 | 6/1980 | Takahashi et al. | 525/170 |
| 4,675,390 | 6/1987 | Bonjouklian et al. | 536/4.1 |
| 4,760,137 | 7/1988 | Robins et al. | 536/24 |
| 4,898,936 | 2/1990 | Ollmann et al. | 536/4.1 |
| 4,931,575 | 6/1990 | Abushanab | 536/1.1 |
| 4,987,224 | 1/1991 | Chu | 536/124 |

OTHER PUBLICATIONS

Chemical Abstracts, vol. 76, No. 7, Issued 14 Feb. 1972, Ciba–Geigy "Antiinflammatory D–Glucofuranose Compounds" see p. 345, col. 2, Abstract No. 345360p, Brit. 1,246,117 (cl. C07D, A61K), 15 Sep. 1971, Swiss Appl. 11 Sep. 1967–25 Apr. 1968.
Chemical Abstracts, vol. 109, No. 5, Issued 1 Aug. 1988, Martin "Intramolecular C–Arylation of 2,3,5–tri–O–Benzyl and 2,3,5–tri–O–(3–Methylbenzyl) Pentofuranose Derivatives" see p. 644, col. 1, Abstract No. 38092p, *Carbohydr. Res.* 1987, 171, 211–22 (Eng).

*Primary Examiner*—John Kight, III
*Assistant Examiner*—Everett White
*Attorney, Agent, or Firm*—Samuels, Gauthier, Stevens & Reppert

[57] ABSTRACT

Enantiomerically pure glycerol derivatives, e.g. S-1,2-O-isopropylidene, S-1,2-O-benzylidene, and R-1,2-O-dibenzyl glycerol, have been prepared from 1,2R-O-protected erythritols in high yields. The latter compounds are easily obtained from erythorbic acid and are useful building blocks in the synthesis of a host of optically active compounds having biological activity.

2 Claims, 4 Drawing Sheets

CHIRAL GLYCEROL DERIVATIVES

This application is a continuation of application Ser. No. 07/852,885 file Mar. 17, 1992, now abandoned, which is a continuation of application Ser. No. 07/505,246 filed Apr. 5, 1990, now abandoned, which is a divisional of application Ser. No. 07/025,624 filed Mar. 13, 1987, now U.S. Pat. No. 4,931,575.

DESCRIPTION OF THE INVENTION

1. Technical Field of the Invention

This invention relates to a process and compounds useful for the preparation of R— and S— glycerol derivatives, common building blocks for a number of chiral natural and synthetic products, from a single intermediate in high yields. Both R— and S— isomers can be prepared by selective cleavage of either the C1–C2 or C3–C4 bonds in a properly protected, and thus chiral, erythritol derivative. In another embodiment, this invention relates to a process and compounds useful for obtaining such building blocks in enantiomerically pure form.

2. Background Art

Chirality, or "handedness", is a term which was first applied by Lord Kelvin to any geometric shape having an image in a plane mirror which cannot be brought to coincide with itself, as with our left and right hands. Atoms to which different ligands are attached at each of three or four valances (e.g., carbon, nitrogen, phosphorus, etc.) form a chiral center, which is a necessary and sufficient condition for the existence of optically active mirror-image isomers known as enantiomers.

Enantiomers show different properties, both physical and chemical, only in a chiral medium, e.g. irradiation with plane or circularly polarized light, reaction with an optically active reagent, solubility in an optically active solvent, or adsorption onto an optically active surface.

The maximum number of stereoisomers that can exist is $2^n$ where n is the number of chiral centers in a molecule. Compounds containing a plurality of chiral centers can also exist as diastereomers, which are stereoisomers that are not mirror images of each other. Diastereomers have similar (but not identical) chemical properties and different physical properties which facilitate separation into their racemic mixtures which can then be resolved by the use of optically active reagents.

Characterization of a particular isomer's configuration is determined by applying a well-known set of sequence rules to assign priorities to the ligands which are attached to the chiral center, after which the molecule is visualized With the lowest priority ligand directed away from the viewer. If proceeding from the highest priority ligand to those of the second and third priority is a clockwise direction, the configuration is specified R; if counterclockwise, S. Because this configuration has no relationship to the direction of optical rotation, a complete name for an optically active compound reveals both configuration and direction of rotation, e.g. (S)-(+)-sec-butyl chloride.

Where compounds contain more than one chiral center, the configuration about each center is specified together with the nomenclature number of the chiral carbon atom, e.g. (2S,3S)- and (2R,3R)- compounds are enantiomers having opposite configurations for each chiral center, whereas (2S, 3S)- and (2S,3R)- compounds would be diastereomers with the same configuration about one chiral center and the opposite configuration about the other.

Stereoisomers are ubiquitous building blocks in nature. For example, (+)-glucose contains five chiral centers which give rise to 32 stereoisomers. Naturally occurring glucose in the alpha-form is the monomeric unit of starch, from which our food ultimately comes, whereas beta-D-glucose is the monomeric unit of cellulose, the framework of plants that synthesize starch.

Glycerol is a simple trihydric alcohol having thousands of uses as an industrial chemical and as a starting material for the preparation of many pharmaceuticals by reactions which involve substitutions Of one or more primary hydroxyl groups in the glycerol molecule. Such a substitution of glycerol (which has a "pro-chiral" center at C2 which is capable of becoming a chiral carbon atom) is a desired starting material for the synthesis of optically active glycerol derivatives. Because the synthesis of chiral compounds from achiral reactants always yields the optically inactive (RS) racemic mixture, the ability to generate a pure enantiomer starting material would effectively multiply the final yield of a desired isomer in products such as those prepared by a reaction that does not involve the breaking of a bond to a chiral center.

One example of a pharmaceutical glycerol derivative is the chiral synthon (chiron) 2,3-O-isopropylidene-L-glycerol or (R)-(−)-2,2-dimethyl-1,3-dioxolane-4-methanol described in K. H. X. Mai and G. Patil U.S. Pat. No. 4,575,558 as an important intermediate for preparing optically active beta-adrenergic agonists and antagonists and as a chiral building block in a number of natural products. The optically active glycerol derivatives used for the preparation of these molecules are derived from D- and L-serine. The presence of the substituted glycerol backbone in such compounds lends itself to synthesis using the methods of the present invention.

J. J. Baldwin and D. E. McClure U.S. Pat. No. 4,588,824 describe a process for preparing the (S)-enantiomer of Mai. et al., (S)-glycerol-1,2-acetonide or (S)-(+)-2,2-dimethyl-1,3-dioxolane-4-methanol by treating 1,2:5,6-di-O-isopropylidene-D-mannitol with lead tetraacetate in an aprotic solvent, reducing the optically active glyceraldehyde reaction product with an alkali metal borohydride and treating the reaction mixture with an ammonia halide to form the (S)-glycerol derivative. The product is a useful intermediate for the preparation of either the (S)— or (R)— enantiomer of epihalohydrins from the same starting material without requiring costly and inefficient racemic resolution procedures.

R. M. Carman and J. J. Kibby describe the preparation of chiral benzylidene derivatives of glycerol in Aust. J. Chem 29:1761–67 (1976) by a method admittedly cumbersome, tedious, and difficult to duplicate.

J. Jarczak et al. have recently reviewed the role of (R)— and (S)— 2,3-O-isopropylideneglyceraldehyde in stereoselective organic synthesis in Tetrahedron Report No. 195, Tetrahedron 142 (2): 447–487 (1986). Starting from the three-carbon glycerol backbone, techniques are described for building to compounds having 20 and more carbon atoms, e.g. lecithins, glycerol-3-phosphates, macrobicyclic polyethers and riboses (page 455); natural products including brefeldin (a sex pheromone), leukotrienes such as LTA4, and prostaglandins (see pages 479–485). The glyceraldehydes undergo many of the same chemical reactions as their corresponding glycerols but are less storage stable due to their tendency to polymerize.

Although the chemistry of L-ascorbic acid has been thoroughly studied, that of its C-5 isomer, D-isoascorbic acid, remains relatively unexplored. The synthetic utility of D-isoascorbic acid is not limited to the preparation of R— and S— glycerol derivatives. It, along with L-ascorbic acid, serves as an attractive precursor for the preparation of new selectively protected chiral erythritols and threitols, which, in their own right, are attractive building blocks in organic synthesis.

Synthetic approaches to 2-deoxy-2-amino-D-threose have been described in a 1982 thesis by David C. J. Wu (Department of Medicinal Chemistry, University of Rhode Island) as a potential synthon for adenosine deaminase inhibitors. However, there is no suggestion that the 3,4-O-isopropylidine-D-erythritol intermediate in that process would be useful as a source of enantiomerically pure R— or S— diastereomers in accordance with the present invention.

DISCLOSURE OF THE INVENTION

Accordingly, it is a general object of the present invention to provide a method for the synthesis of optically active glycerol derivatives wherein either the (R)— or (S)— enantiomer can be prepared from the same starting material.

Another object of the present invention is to provide a method for the utilization of 1,2-O-protected (and thus chiral) erythritol derivatives as chiral synthons or chirons.

An additional object of this invention is to provide a method and compounds useful therein whereby these same chiral erythritol derivatives can be used as a building block to which one carbon fragments in the proper oxidation state can be added to provide enantiomerically pure compounds such as 3,5-di-O-protected 2-deoxypentofuranoses and their glycosides.

A further object of the present invention is to provide a process for the preparation of optically active chiral phosphorylated acyclic nucleosides having chemotherapeutic activity, especially cytotoxic or antiviral activity, e.g. derivatives of acyclovir.

A more particular object of the present invention is to provide a method for the preparation of optically active chiral platelet-activating factor (PAF) and other fatty acid ethers and esters.

Upon study of the specification and appended claims, further objects, features and advantages of the present invention will become more fully apparent to those skilled in the art to which this invention pertains.

BEST MODE FOR CARRYING OUT THE INVENTION

Briefly, the above and other objects, features and advantages of the present invention are attained in one aspect thereof by providing a process for preparing a R-2,3-O-protected glyceraldehyde, which comprises:

a) selecting a corresponding 2R,3S-1,2-O-protected butane 1,2,3,4-tetrol;

b) reacting said tetrol under conditions which preserve the cyclic acetal 1,2-O-protecting group while cleaving the C3–C4 bond to form enantiomerically pure R-2,3-O-protected glyceraldehyde; and c) recovering said enantiomerically pure R-2,3-O-protected glyceraldehyde.

In a second aspect of this invention, enantiomerically pure 3,5-di-O-protected 2-deoxypentofuranoses and their glycosides selected from the group consisting of 2-deoxy-L-xylose, 2-deoxy-L-ribose, 2-deoxy-D-xylose and 2-deoxy-D-ribose, are prepared by a process which comprises:

a) selecting a corresponding 4,5-O-arylidine-3-O-protected 3,4,5-trihydroxy pentanonitrile of Formula 7, 8, 9 or 10 as shown in FIG. 3 wherein Ar is carbocyclic aromatic and R is an aliphatic, cycloaliphatic, arylkl (e.g. benzyl), silyl or the like O-protecting group as defined herein which is more stable to cleavage than CN; and b) reducing the 4,5-O-arylidine-3-O-protected 3,4,5-trihydroxy pentanonitrile to form a corresponding D- or L- sugar of Formula 11, 12, 13 or 14, respectively, as shown in FIG. 3.

In a third aspect of this invention which can be schematically seen in FIG. 2, there is provided a method for the preparation of optically active chiral phosphorylated acyclic nucleosides or platelet activating factor (PAF) analogues.

The potential utility of this work is evident in natural products and drug synthesis. For example, dihydroxypropoxymethyl guanine (DHPG) is a potent antiviral drug which has a glycerol backbone that must be phosphorylated at only one site by a viral enzyme before exerting its anti-herpetic action. Therefore DHPG becomes ineffective if the target virus lacks a phosphorylating enzyme. Therefore a logical solution to this problem could be reached by chemical, rather than enzymatic phosphorylation of DHPG. This, however, unlike enzymatic phosphorylation, produces a racemic (50:50) mixture of drug isomers where only one isomer has biological activity. Being able to produce the right (active) isomer is therefore an attractive process, both scientifically and economically; such a process is provided in a fourth aspect of this invention.

In a fifth aspect, the present invention provides a method for preparing isomerically pure (R)— or (S)-enantiomers of platelet-activating factor (PAF) and related compounds.

BRIEF DESCRIPTION OF THE DRAWINGS

This invention Will be more fully appreciated by those skilled in the art to which it pertains by reference to the accompanying Drawings, wherein.

DETAILED DESCRIPTION

Referring to the Formulae of FIGS. 1 through 4, R, R' and R" are each aliphatic or cycloaliphatic. Aliphatic or cycloaliphatic is preferably of up to six carbon atoms, e.g., alkyl, alkenyl, alkynyl, cycloalkyl or cycloalkenyl. Suitable alkyl groups include but are not limited to methyl, ethyl, n-propyl, isopropyl, n-butyl, isobutyl, sec-butyl and tert.-butyl. Suitable alkenyl groups include but are not limited to vinyl, 2,2-dimethylvinyl, allyl, dimethylallyl, 1-propenyl, 1-butenyl, 2-butenyl, 3-meththyl-2-butenyl, 1-pentenyl and 2-pentenyl. Suitable alkynyl groups include but are not limited to propynyl, butynyl and pentynyl. Suitable cycloalkyl groups include but are not limited to cyclopropyl, cyclobutyl, cyclopentyl and cyclohexyl optionally substituted, e.g., by alkyl or alkenyl of up to four carbon atoms to form cycloalkylalkyl or cycloalkylalkenyl, e.g., cyclopropylmethyl. Suitable cycloalkenyl groups include but are not limited to cyclobutenyl, cyclopentenyl and cyclohexenyl optionally substituted, e.g., by alkyl or alkenyl of up to four carbon atoms to form cycloalkenylalkyl orcycloalkenylalkenyl, e.g., cyclobutenylethyl.

Figure 3:
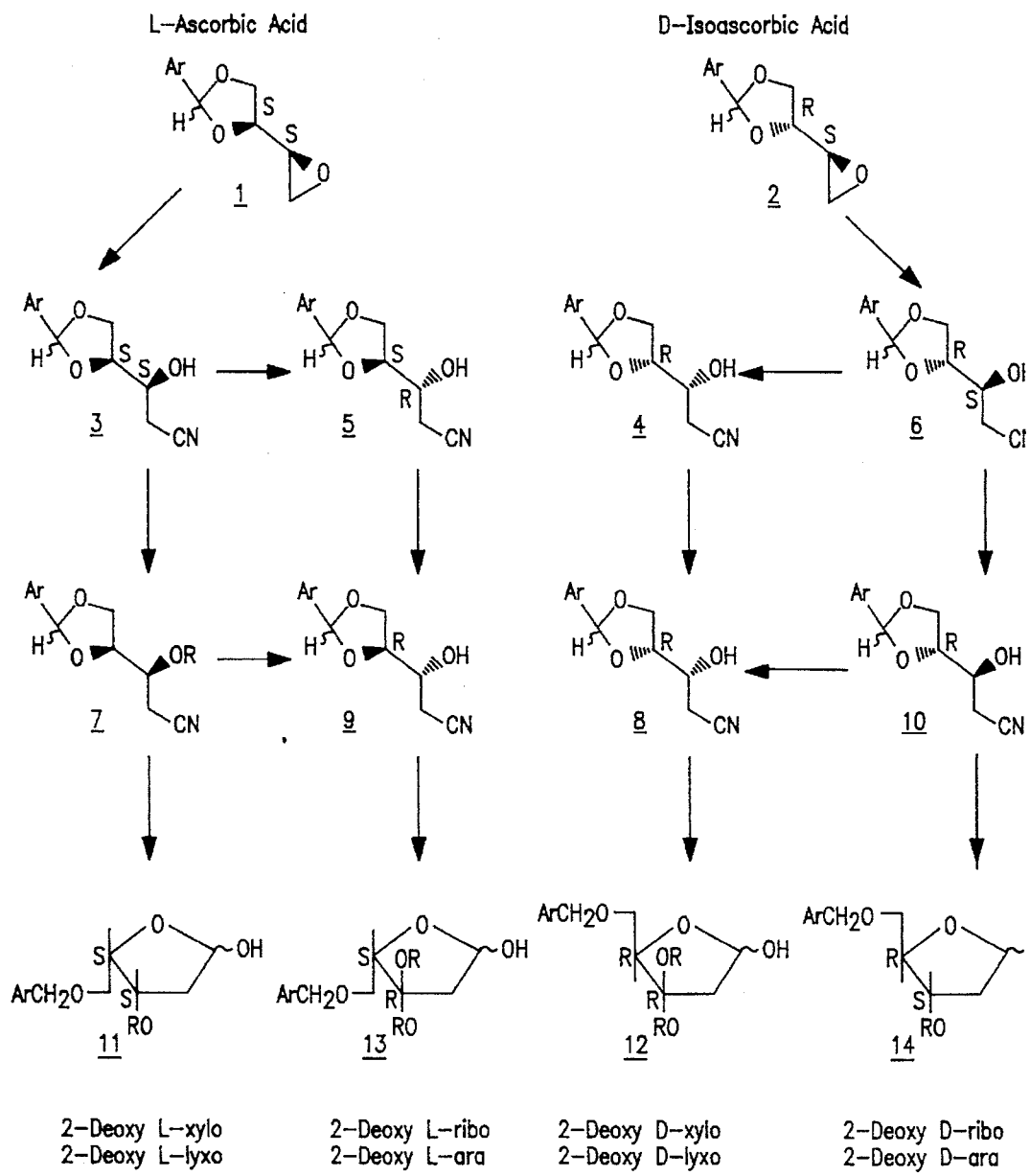
FIG. 3 schematically illustrates the reaction sequences and intermediates formed according to a process of this invention for preparing enantiomerically pure 3,5-di-O-protected 2-deoxypentofuranoses and their glycosides.
Figure 4:
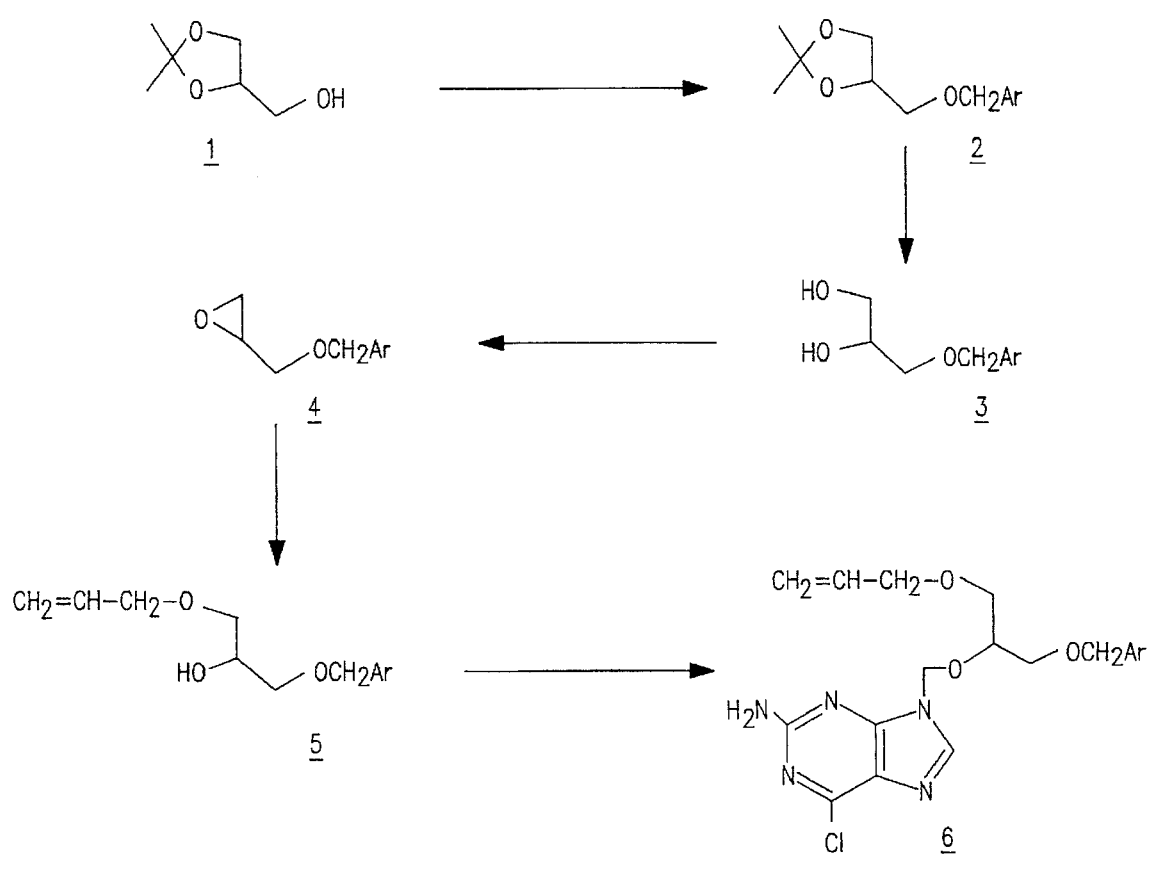
FIG. 4 schematically illustrates the reaction sequences and intermediates formed in a process of the present invention for the preparation of analogs of acyclovir.

In FIGS. 3 and 4, Ar is carbocyclic aromatic. Carbocyclic aromatic can be aryl or alkaryl. Carbocyclic aryl is preferably phenyl, naphthyl or substituted phenyl; carbocyclic alkaryl is preferably alkylphenyl or substituted alkylphenyl, e.g., tolyl. Suitable substituents of the carbocyclic aromatic group are 1–3 lower alkyl groups, e.g., methyl; 1–3 lower alkoxy groups, e.g., methoxy or ethoxy; and 1–3 halogen atoms, e.g., fluorine (including trifluoromethyl), chlorine or bromine. Suitable substituted carbocyclic aromatic groups include but are not limited to o-, m- or p- tolyl; o-, m- or p-methoxyphenyl; o-, m- or p-fluorophenyl; o-, m- or p-chlorophenyl; and alpha- or beta- naphthyl.

Figure 1:
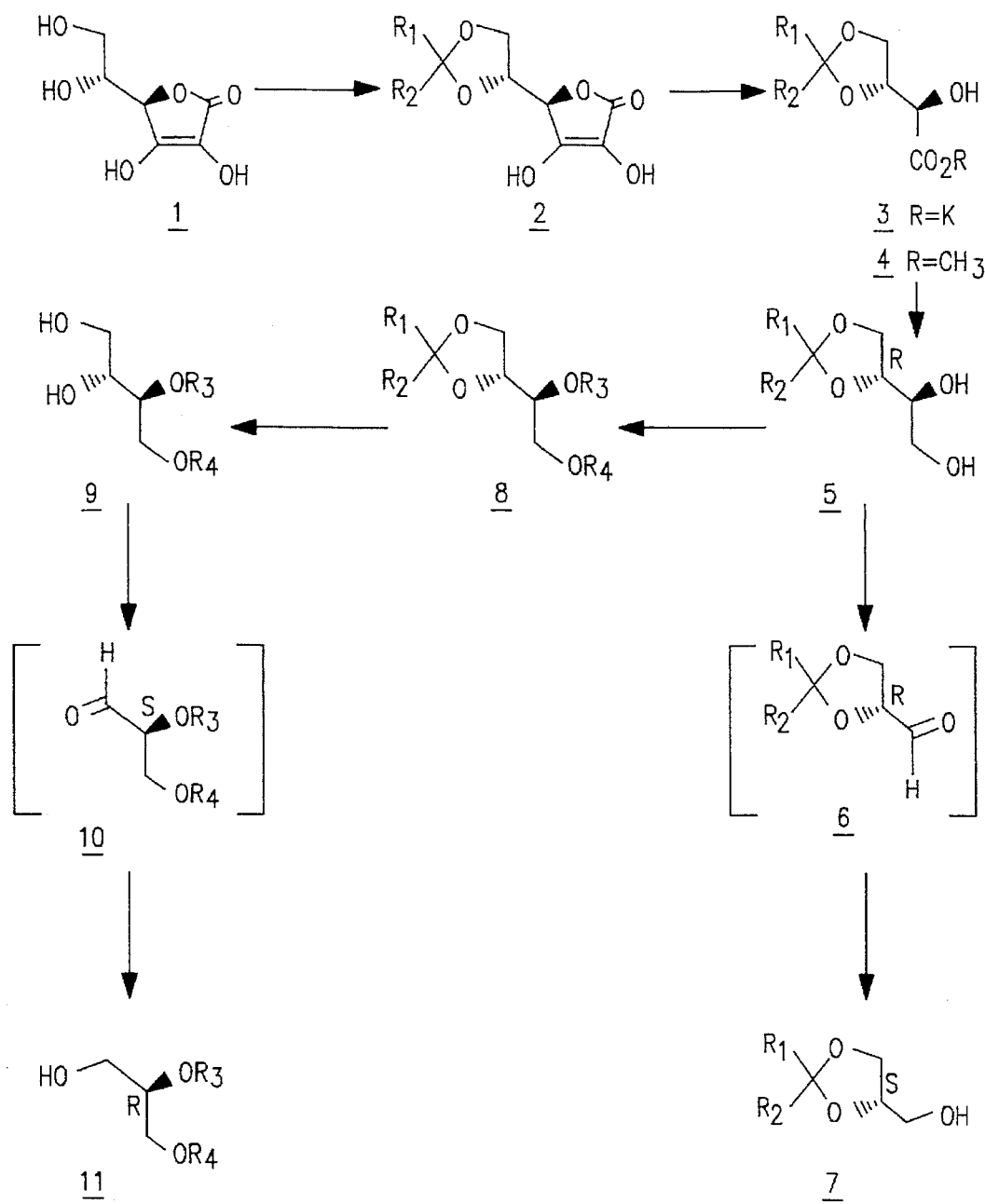
FIG. 1 is a schematic illustration of the reaction sequences and intermediates formed according to a process of the invention for preparing enantiomerically pure isomers of either the (R)— or (S)— configuration from the same starting material.

In a first aspect of this invention, enantiomerically pure R-isomers of glycerol are prepared by selective cleavage of the C1–C2 bonds of chiral erythritol derivatives which are 1,2,3,4-tetra-O-protected-butane-1,2,3,4-tetrols of Formula 8 in FIG. 1 in which the C1–C2 protecting groups are susceptible to cleavage under conditions which do not cleave the C3–C4 protecting groups.

Suitable hydroxyl masking groups are well known in the art and include but are not limited to an acyl group (e.g., an alkanoyl group of 2–5 carbon atoms such as acetyl, propionyl and butyryl, or an aroyl group such as benzoyl), an arylmethyl group (e.g., benzyl), and alkylsulfonyl group (e.g., an alkylsulfonyl of 1–4 carbon atoms such as methylsulfonyl or ethylsulfonyl), an aralkylsulfonyl group (e.g., benzylsulfonyl) or an arylsulfonyl group (e.g., phenylsulfonyl or p-toluylsulfonyl).

It is necessary that the chemical reactivity of the protecting groups (if any) at positions 1 and 2 be different from those at positions 3 and 4. Such arrangements are known in the art and have been described, for example, by Dr. Theodora W. Greene in Protective Groups in Organic Synthesis, John Wiley and Son, New York (1981). For example, silyl ethers, alkoxy alkyl ethers, aryloxy alkyl ethers, acetals, ketals and THP cyclic ethers (cleaved by mild acidic hydrolysis) or esters (cleaved by basic hydrolysis) can be prepared to protect isolated hydroxyl groups; 1,2-diols can be protected as cyclic ethers (e.g., alkylidene, arylidene, etc., cleaved by acidic hydrolysis) or as cyclic esters, e.g., cyclic carbonates and cyclic boronates (cleaved by basic hydrolysis). Benzyl or substituted benzyl masking groups can be used when cleavage by hydrogenolysis is desired.

In a second aspect of this invention, enantiomerically pure S-isomers of glycerol are prepared by selective cleavage of the C3–C4 bonds of chiral erythritol derivatives of Formula 5 in FIG. 1 which are 1,2-di-O-protected-butane-1,2,3,4-tetrols.

The second aspect of this invention involves a reductive opening of an unsymmetrical 2-aryl 1,3-dioxolane (arylidene) ring, e.g., using sodium cyanoborohydride. The application of this well described literature procedure to 1,2-O-arylidene glycerol derivatives allows the preparation of a primary benzyl ether and a free secondary hydroxyl group at positions one and two of glycerol. Since chirality at C-2 is determined by atomic number priorities of its substituents, it can be easily seen that manipulation of these priorities, and thus chirality at C-2, can be easily accomplished by selective deblocking at C-1 or C-3.

When the hydroxyl-masking group is of the acyl type such as alkanyl removal can be accomplished by alkaline hydrolysis using aqueous sodium hydroxide, ammonia in methanol or sodium methylate in methanol. When the hydroxyl-masking group is isopropylidene, cyclohexylidene, benzylidene, tetrahydropyranyl or methoxycyclohexyl, removal can be accomplished by mild hydrolysis using diluted hydrochloric acid or aqueous acetic acid. When the hydroxyl-masking group is benzyl, p-toluyl or the like, removal can be achieved by catalytic hydrogenolysis in the presence of palladium on carbon.

As illustrated in FIG. 1, starting with D-isoascorbic acid (1a) 1,2R-O-isopropylidene erythritol (5a) has been prepared from 5,6-O-isopropylidene D-isoascorbic acid (2a); 1H nmr (acetone-d6):delta 1.3 and 1.37 (two 3H, s), 3.6–3.9 (2H, 4.37 (1H, m), 4.75 (1H, d, J=3 Hz), 8.4 (2H, br s).

Both 5,6-O-isopropylidene and 5,6-O-benzylidene D-isoascorbic acid (2a and 2a) were oxidatively cleaved without purification. Potassium 3,4-O-isopropylidene-D-erythronate (3a) was separated from inorganic by-products by extraction with anhydrous ethanol. Treatment of 3a with iodomethane in refluxing acetonitrile gave methyl ester 4a [alpha] $_D$–23.87 (C 4.84, EtOH); 1H nmr (CDCl$_3$): delta 1.33 and 1.40 (two 3H, s), 3.6 (1H, s), 3.73 (3H, s) 3.95 (2H, d, J=6 Hz), 4.18 (2H, m) in 76% yield from D-isoascorbic acid. Compound 4b was obtained similarly as a mixture of diastereomers showing benzylidene protons at delta 5.7 and 6.0 ppm.

Lithium aluminum hydride reduction of 4a in ether gave diol 5a as an oil in 82% yield; [alpha] $_D$+5.83 (C 8.28, EtOH); 1H nmr (DMSO-d6); delta 1.25 and 1.30 (two 3H, s), 3.21–4.0 (6H, m), 4.61–4.93 (2H, m). Likewise diol 5b was obtained as a diastereomeric mixture. S-1,2-O-isopropylidene glycerol (7a) was obtained from 5a by cleavage with sodium periodate and reduction of the resulting R-aldehyde (6) with sodium borohydride. The S-1,2-O-benzylidene isomer (7b) was obtained in an identical manner from 5b; 1H nmr (CDCl$_3$) : delta 2.4 (1H, br s), 3.5–4.4 (5H, m), 5.73, 5.8 (two 1/2H, s, diastereomeric benzylidene protons), 7.2–7.5 (5H, m).

R-1,2-Di-O-benzylglycerol 11 was then obtained from diol 5a. Benzylation of 5a (NaH, DMF) furnished the dibenzyl derivative (8); [alpha] $_D$+16.77 (C 2.96, EtOH); 1H nmr (CDCl$_3$): delta 1.27 and 1.32 (two 3H, s), 3.52 (3H, m), 3.88 (3H m) 4.37 (2H s) 4.52 (2H, ABq, J=14 Hz) 7.16 (10H, s). Cleavage of the ketal (90% aqueous ethanol, IR-120 Plus) afforded diol 9: [alpha] $_D$+4.21 (C 1.46, EtOH). Successive treatment of 9 with sodium periodate and sodium borohydride furnished glycerol 11; [alpha] $_D$+1.31 (C 3.21, EtOH), lit. 16+3.8 (neat); 1H nmr (CDCl$_3$): delta 2.2 (1H, br s), 3.43–3.83 (5H, m), 4.46 (2H, s), 4.46–4.73 (2H, ABq, J=12 Hz), 7.2–7.36 (10H, m).

In a third aspect of this invention, it has been found that these same chiral erythritol derivatives can be used as a building block to which one carbon fragment in the proper oxidation state can be added to provide enantiomerically pure compounds-such as 3,5-di-O-protected-2-deoxypentofuranoses and their glycosides.

Briefly, this can be achieved according to the present invention by a reaction sequence using a 1,2-O-benzylidinebutane 1,2,3,4-tetrol starting material in which the unprotected 3- and 4-hydroxyl groups are converted to an epoxide, e.g. via the Mitsunobu reaction described in a review appearing in Synthesis 1:1–28 (1981). This reaction involves reaction with diethyl azodicarboxylate and triphenylphosphine to form, for example, a 2S,3R-1,2-anhydro-3,4-arylidene-butane-1,2,3,4-tetrol. Chiral 1-O-benzyl glycerol can alternatively be used to form the corresponding glycerol epoxide, e.g. according to the procedure described by S. Takano et al. in Synthesis 116 (1983). Inversion can be accomplished, for example, using the techniques described by Mitsunobu in Bull. Chem. Soc. Jap. 49:510 (1976) or by H. Redlich and W. Francke in Agnew. Chemie. Int'l. Ed. Eng. 19:630 (1980) to form the 2S,3S-1,2-anhydro-3,4-arylidene-butane-1,2,3,4-tetrol isomer if desired.

The resultant epoxide is then reacted with a carbon atom source which undergoes an addition reaction with the epoxide group (e.g. a cyano group) to open the epoxide ring and form a corresponding 1-substituted butane-2,3,4-triol having five carbon atoms, e.g. 4R,3S-4,5-O-benzylidine-3,4,5-trihydroxy pentanonitrile. The only requirement for such a carbon atom source appears to be the ability to form a negatively charged carbon atom. Several such reactants are known in the art and include but are not limited to the presently preferred cyanide, dithianes and arylmethyl sulfoxides.

Also suitable as carbon atom sources are thiazoles, e.g. as described by A. Dondoni et al. in Agnew. Chem. Int. Ed. Eng. 25:835 (1986); dithianes and dithiolanes (which can be considered as masked formaldehydes) as described by B. T. Grobel et al. in Synthesis 357–402 (1977); oxazolines-, e.g. as described by A. I. Meyers et al. in Agnew. Chem. Int. Ed. Eng. 15:270–281 (1976); methyl methylthiomethyl sulfoxide, as described by K. Ozura et al. in Tetrahedron Lett. 3653 (1974); etc. Such other suitable groups are generally less preferred because they require an additional subsequent reaction, e.g. the addition of an oxazole or thiazole group requires subsequent reduction, while the addition of a sulfoxide requires a Pummerer rearrangement with acetic anhydride, e.g., as described by W. E. Parham et al., in J. Org. Chem. 33:4150–4154 (1968).

The resultant intermediate compounds, e.g. 4R,3S-4,5-O-benzylidine-3,4,5-trihydroxy pentanonitrile, contain two chiral carbon atoms and are accordingly capable of existing in four potential isomeric forms. For two of these isomeric forms, it is convenient to invert the single unprotected hydroxyl group at the 3-position using known techniques prior to masking it by known techniques such as those described herein.

The added carbon moiety is then reduced, e.g. a cyano group added by reaction With a nitrile can be reduced, preferably using DIBAL (diisobutyl aluminum hydride); these compounds have been found to be particularly useful in cleaving benzylidine acetals in both cleaving the O-benzylidine hydroxyl protecting groups and in converting them into a benzyl ether, as has been described by S. Takano et al. in Chemo Letters 1593–1596 (1983) published by the Chemical Society of Japan. Other versions of such a reaction have been described by E. Winterfeldt in Synthesis 617–626 (1975). Other carbon fragment moieties can be reduced by techniques likewise known in the art, e.g. see Fieser and Fieser, Reagents for Organic Synthesis, pages 260–262 (1967).

For those cases wherein the added carbon fragment does not require further reduction, a broader choice of benzylidene acetal reducing agent is available, e.g. $LiAH_4$/ $AlCl_3$ as described by J. Gelas in Adv. Carbohydr. Chem. Biochem. 59:39 71–155, especially at pages 121–137 (1981) or $NaCNBH_3$/HCl as described by P. J. Garegg et al. in Carbohydr. Res. 108: 97–101 (1982).

As previously indicated, reduction of the 3-O-protected-4,5-di-O-protected derivative, e.g. 4R, 3S-4,5-O-benzylidine-3,4,5-trihydroxy pentanonitrile, with DIBAL simultaneously reduces the nitrile group to form a corresponding 3,5-di-O-protected-2-deoxy-pentofuranose or a glycoside thereof; the D-sugars are obtained when the intermediates have been prepared starting from isoascorbic acid in the reaction scheme and the L-sugars from ascorbic acid as the original starting material, the L— or D— configuration of the acid being determined by that of the C5 carbon atom (which is the C4 carbon atom in the starting tetrol).

Preferably the base used in this aspect of the present invention is a nucleoside base selected from the group consisting of substituted or unsubstituted adenine, guanine, thymine, uracil and hypoxanthine. The base can be unsubstituted or substituted by halogen, seleno, thio, amino, alkylamino, arylamino, oxo, alkyl, aryl, alkoxy, aryaloxy, alkoxyaryl or arylalkoxy, e.g. guanine substituted at the 6- or 8- position, especially by a halogen, e.g. chlorine; 6-chloroguanine is especially preferred. The reaction scheme for this aspect of the present invention is shown in FIG. 2, with the intermediates therein shown as Formulae 15–17 and the analogues themselves as Formula 19.

Figure 2:
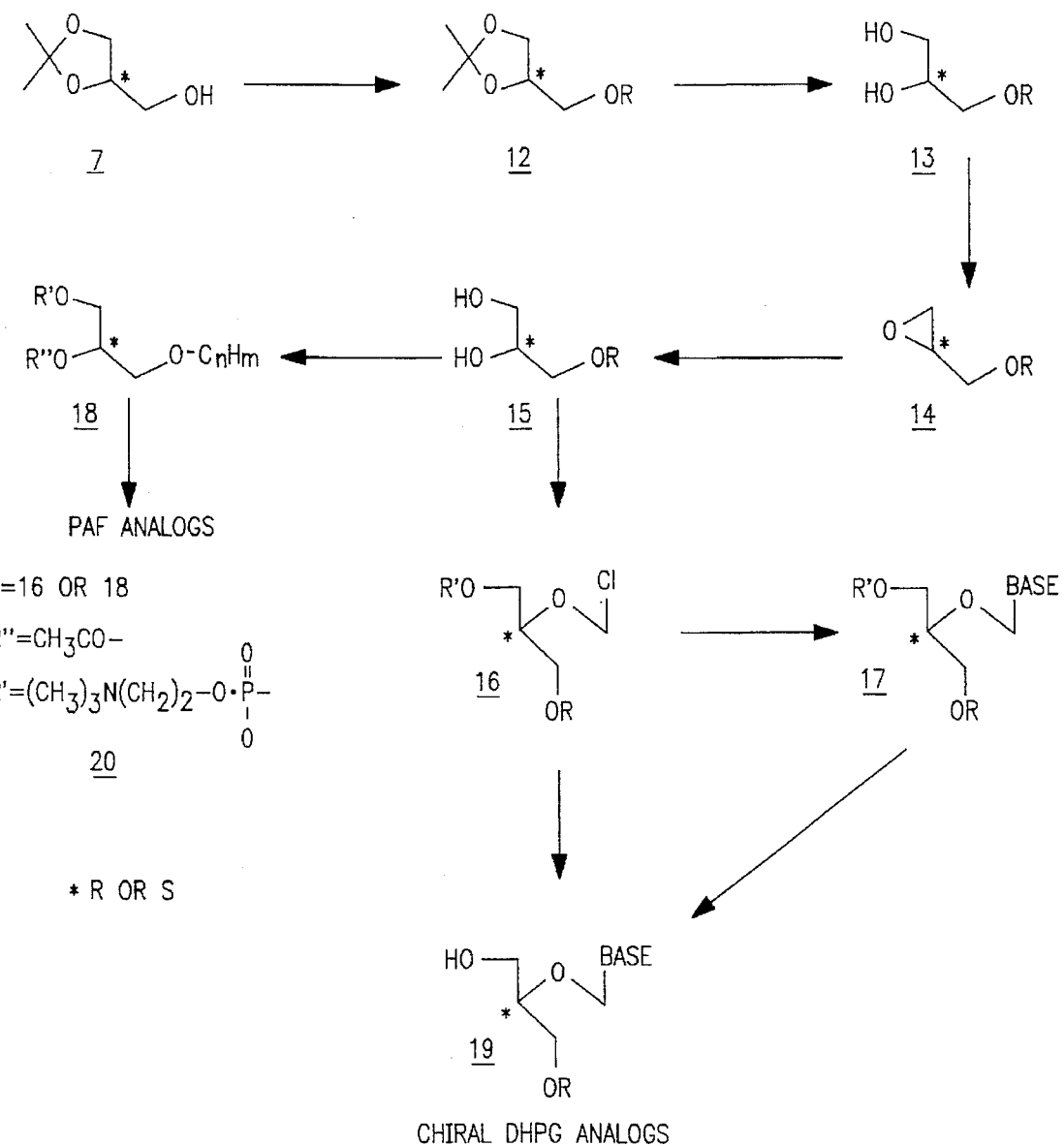
FIG. 2 schematically illustrates the reaction sequences and intermediates formed in a process of the present invention for the preparation of optically active (a) chiral phosphorylated acyclic nucleosides having chemotherapeutic activity, especially cytotoxic or antiviral activity (left side), or alternatively (b) chiral PAF and other fatty acid ethers and esters (right side)

In a fifth aspect, the present invention provides a method for preparing isomerically pure (R)— or (S)-enantiomers of Formula 18 in FIG. 2, wherein R' and R" have the above-indicated values and R is a group of the formula CnHm wherein n is an integer from 1–24, preferably 12–20, and m is equal to 2n+1, 2n−1, 2n−3, 2n−5 or 2n−7 provided that R"O is stable against cleavage under conditions wherein RO or R'O can be cleaved.

Preferred values in the above formula are those wherein n in 12–20 and m is 2n+1, 2n−1 or 2n−3, especially where n is 14–18 and particularly where the product is in the form of a mixture of enantiomers in which n has a plurality of the above-indicated values, e.g. wherein n=16 and 18 as in palmityl and the product is platelet activating factor.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the following Examples, the temperatures are set forth uncorrected in degrees Celsius; unless otherwise indicated, all parts and percentages are by weight.

Melting points were determined on a Thomas-Hoover melting point apparatus (capillary method) and are uncorrected. IR spectra were obtained on a Beckman IR-8 spectrophotometer. Optical rotations were measured on a Perkin-Elmer Model 141 polarimeter. The 1H NMR spectra were recorded on a Varian EM-390 MHz spectrometer, and $CDCl_3$ was used as solvent unless otherwise indicated. Chemical shifts are expressed in parts per million with respect to $Me_4Si$. TLC was performed on precoated (0.25 mm) silica gel 60F-254 plates purchased from EM Laboratories, Inc., and separated materials were detected with ultraviolet and/or by spraying with 20% sulfuric acid followed by charring. EM silica gel 60 (70–230 mesh ASTM) was employed for routine column chromatography and 230–400 mesh ASTM for flash chromatography. The term "usual workup" means washed with water, dried with magnesium sulfate, filtered and evaporated. Evaporations were performed with a Buchi Rotavapor at 40° C. unless otherwise stated. Elemental analyses were performed by M-H-W-Laboratories., Phoenix, Ariz.

EXAMPLE 1

This Example illustrates the preparation of alky-protected chiral glycerchiral glycerol derivatives.

To a suspension of 1,2R-O-isopropylidene erythritol (0.012 mol) in distilled water (15 ml) containing sodium phosphate (0.123 g) was added sodium metaperiodate (2.72 g, 0.013 mol) keeping the temperature below 35° C. The suspension was stirred at room temperature for 15 min. Sodium iodate began to precipitate and the addition of methanol (15 ml) completed the precipitation. The solid was filtered off, washed with methanol (5 ml×2) and was discarded. A sodium phosphate buffer (8 ml) was added to the filtrate which was cooled in an ice bath. Sodium borohydride (0.61 g, 0.016 mol) was added in small portions in about 30 min. (foaming occurs), and stirring was continued at room temperature for 3 hrs. Excess sodium borohydride was destroyed with acetone (3 ml). Filtration evaporation gave an oil which was partitioned between a saturated solution of sodium chloride and chloroform. Drying of the organic layer over magnesium sulfate followed by evaporation gave the product in 80% yield; [alpha] $_D$=−11.7 (c=1.03, MeOH)

EXAMPLE 2

This Example illustrates the preparation of aryl-protected chiral glycerol derivatives.

Starting with 3,4-S-O-dibenzyl-erythritol, R-1,2-O-Dibenzylglycerol was obtained in an identical manner to the procedure described above in 64% yield;

[alpha] $_D$=+1.31 (c=3.21, EtOH)

EXAMPLE 3

Preparation of 2R,3S-3,4-epoxy-1,2-O-benzylidene-butane-1,2-diol.

8 grams (0.038 mole) 2R,3S-1,2-O-benzylidene-butane-1,2,3,4-tetrol were reacted with 0.0438 mole triphenyl phosphine in the presence of 0.0438 mole diethylazidodicarboxylate (DEAD) in 88 ml benzene with heating. After the addition, the benzene was removed and the residue distilled (0.04 mm) to give a 7.003 gram mixture of the benzylidene epoxide and H$_2$DEAD in a ratio 21:33. Ethyl ether was added to precipitate the H$_2$DEAD, which was collected. A mixture of the benzylidene epoxide and H$_2$DEAD was obtained after removing ether from the filtrate.

The undistillable residue was dissolved in chloroform and absorbed on 20 grams of silica gel, 230–400 mesh. This was eluted with a 10% ethyl acetate (EtAc) in hexane, giving 0.339 gram of the epoxide. Two fractions were combined and chromatographed on silica gel; elution with 10% EtAc in hexane gave 3.3831 gm (46.3%) of the pure benzylidene epoxide.

EXAMPLE 4

Preparation of 2S,3S-3,4-epoxy-1,2-O-benzylidene-butane-1,2-diol.

0.1567 mole of 2S,3S-1,2-O-benzylidene-butane-1,2,3,4-tetrol was reacted with 0.18 mmole triphenyl phosphine and 0.58 mmole DEAD in 362 ml dry benzene. After addition of reactants, benzene was removed and the residue heated at 145° C. and 0.15 mm to give 2.3 grams of the benzylidene epoxide. The unfilterable product was dissolved in chloroform and absorbed on 440 grams of silica gel, which was charged on top of a silica gel column (60–230 mesh, 150 grams) and eluted with 5% EtAc in hexane, giving 8.4269 grams of the benzylidene epoxide. Combined with a second elution, the total yield was 10.4169 grams or 35%.

EXAMPLE 5

This example shows addition of a carbon fragment to the epoxide.

0.0113 mole of 2R, 3S-3,4-epoxy-1,2-O-benzylidene-butane1, 2-diol was reacted with 0.0113 mole KCN and 0.0104 mole MgSO$_4$. 7H$_2$O in 3.6 grams of water. The crude 2R, 3S-4,5-O-benzylidene-3-hydroxy-pentonitrile product was chromatographed over 30 grams of silica gel, gave four spots upon sequential elution in 10% EtAC in hexane (two samples) and 20% EtAC in hexane (the next two samples). 1.7480 grams of the desired product was obtained, giving a yield of 78.9% based on the starting materials recovered.

EXAMPLE 6

This example shows the addition of a benzyl group.

1.094 mmole of 2R,3S-4,5-O-benzylidene-3-hydroxy-pentanonitrile in 1.5 ml of dry dimethylformamide (DMF) was reacted with 1.20 mmole NaH and 1.117 mmole of benzyl bromide in 0.5 ml of dry DMF. NaH was pre-washed with benzene and 15 ml of dry DMF added. To this was added the cyano alcohol in 1.5 ml of dry DMF. After 5 minutes of stirring, a solution of benzyl bromide in 0.5 ml DMF was added slowly and stirring continued for three quarters of an hour. The reaction mixture was poured into 10 ml of buffer and extracted with ether (4×20 ml). The extract was washed with water (6×10 ml) and dried over MgSO$_4$. Evaporation of ether gave 0.2608 grams of crude product, which showed three spots upon chromatography, i.e., benzyl bromide, starting material and the benzylated cyano compound.

The product was chromatographed over silica gel and eluted with hexane giving benzyl bromide. Further elution with 10% EtAc in hexane gave 1.085 gram (32.1%) of 2R,3S-3-O-benzyl-4-5-O-benzylidene pentanonitrile, the structure of which was confirmed by both NMR and IR.

The preceding examples can be repeated with similar success by substituting the generically or specifically described reactants and/or operating conditions of this invention for those specifically used in the examples. From the foregoing description, one skilled in the art to which this invention pertains can easily ascertain the essential characteristics thereof and, without departing from the spirit and scope of the present invention, can make various changes and modifications to adapt it to various usages and conditions.

Industrial Applicability

As can be seen from the present specification and examples, the present invention is industrially useful in providing a process and compounds useful as intermediates for the preparation of R— and S— glycerol derivatives, common building blocks for a number of chiral natural and synthetic products, from a single intermediate in high yields.

What is claimed is:

1. A process for preparing an enantiomerically pure 2-deoxy pentofuranose selected from the group consisting of 2-deoxy-L-xylose, 2-deoxy-L-ribose, 2-deoxy-D-xylose and 2-deoxy-D-ribose, which comprises:

(a) selecting 4,5-O-arylidine-3-O-protected 3,4,5-trihydroxy pentane derivatives of the Formulae

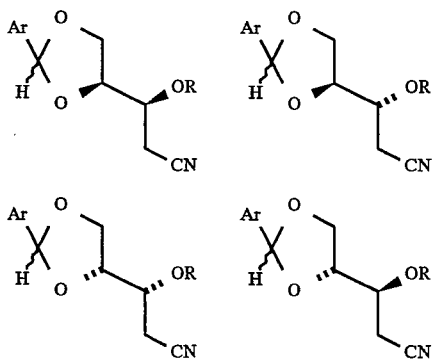

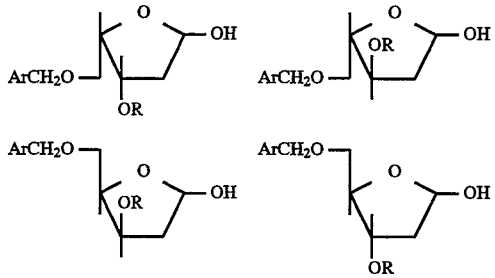

wherein Ar and R are each an O-protecting group wherein Ar is an aromatic or a substituted aromatic selected from the group consisting of aryl; alkaryl; o-, m- or p-tolyl; o-, m- or p-methoxyphenyl; o-, m- or p-chlorophenyl; or alpha- or beta-naphthyl, the substituents selected from the group consisting of 1–3 lower alkyl groups, 1–3 lower alkoxy groups or 1–3 halogen atoms and R is selected from the group consisting of an aliphatic, cycloaliphatic, alkaryl or silyl; wherein the aliphatic or cycloaliphatic is preferably of up to six carbon atoms;

b) reducing with an alkali metal borohydride the pentane derivative to form 3,5-di-O-protected-2-deoxy pentanofuranose having the same chirality as the pentane, of the Formulae separating by filtration a selected enantiomerically pure 2-deoxy pentofuranose; and recovering by chromatographic elution said separated 2-deoxy pentofuranose.

2. The process of claim 1 wherein the aryl is selected from the group consisting of phenyl, naphthyl or substituted phenyl and the alkaryl is selected from alkylphenyl or substituted alkylphenyl; the substituents are selected from the group consisting of 1–3 lower alkyl groups, 1–3 lower alkoxy groups, or 1–3 halogen atoms.

* * * * *